United States Patent
Morris et al.

(10) Patent No.: US 6,488,651 B1
(45) Date of Patent: Dec. 3, 2002

(54) MULTIPLE PART MANUAL DISPENSING SYRINGE

(75) Inventors: David Paul Morris, Valencia, CA (US); Nguyen Thai Dang, Torrance, CA (US)

(73) Assignee: PRC-DeSoto International, Inc., Glendale, CA (US)

( * ) Notice: Subject to any disclaimer, the term of this patent is extended or adjusted under 35 U.S.C. 154(b) by 0 days.

(21) Appl. No.: 09/529,780
(22) PCT Filed: Oct. 16, 1998
(86) PCT No.: PCT/US98/21909
§ 371 (c)(1), (2), (4) Date: Apr. 19, 2000
(87) PCT Pub. No.: WO99/20562
PCT Pub. Date: Apr. 29, 1999

Related U.S. Application Data

(60) Provisional application No. 60/062,846, filed on Oct. 20, 1997.

(51) Int. Cl.⁷ .............................................. A61M 37/00
(52) U.S. Cl. ....................................................... 604/89
(58) Field of Search ................................ 604/181, 183, 604/184, 187, 191, 199, 200–206, 82, 83, 89, 87, 91, 411–416, 218; 222/83, 85

(56) References Cited

U.S. PATENT DOCUMENTS

| | | |
|---|---|---|
| 2,166,437 A | 7/1939 | Howie et al. .................. 259/47 |
| 3,153,531 A | 10/1964 | Cook .......................... 259/113 |
| 3,164,303 A | 1/1965 | Trautmann .................. 222/190 |
| 3,195,778 A | 7/1965 | Coates |
| 3,217,946 A | 11/1965 | Cook .......................... 222/386 |
| 3,437,242 A | 4/1969 | Poitras ....................... 222/135 |
| 3,475,010 A | 10/1969 | Cook et al. ................... 259/47 |
| 4,371,094 A | 2/1983 | Hutter, III ...................... 222/1 |
| 4,966,468 A | 10/1990 | Brüning ....................... 366/333 |
| 5,328,462 A | 7/1994 | Fischer ......................... 604/82 |
| 5,522,804 A | * 6/1996 | Lynn .......................... 604/191 |

FOREIGN PATENT DOCUMENTS

| | | |
|---|---|---|
| WO | WO 88/09679 | 12/1988 |

* cited by examiner

Primary Examiner—Anhtuan T. Nguyen
Assistant Examiner—Ann Y Lam
(74) Attorney, Agent, or Firm—Finnegan, Henderson, Farabow, Garrett & Dunner, L.L.P.

(57) ABSTRACT

A syringe (10) includes a tube (12) defining a chamber (16) with a dispensing opening (18). A plunger (20) is slidably mounted in the tube and is initially positioned at the end (24) of the chamber opposite the dispensing opening. A dasher (26) having an opening (34) is positioned within the chamber at an intermediate point. A cylindrical barrier (40) is detachably secured to the dasher (26). Thus, with the barrier secured to the dasher, the barrier and dasher sealingly engages the tube dividing it into two subchambers (44, 46). An elongated rod (52) extends through openings (54, 56) in the plunger and the barrier and is secured to the dasher. Rotation of the rod detaches the barrier from the dasher establishing communication between the subchambers. A locking sleeve (62) frictionally secures the rod and the plunger together when the rod is moved to a retracted position (FIG. 4). Furthermore, optionally the rod is hollow (FIG. 9) and defines a third subchamber (80) containing a third liquid.

13 Claims, 4 Drawing Sheets

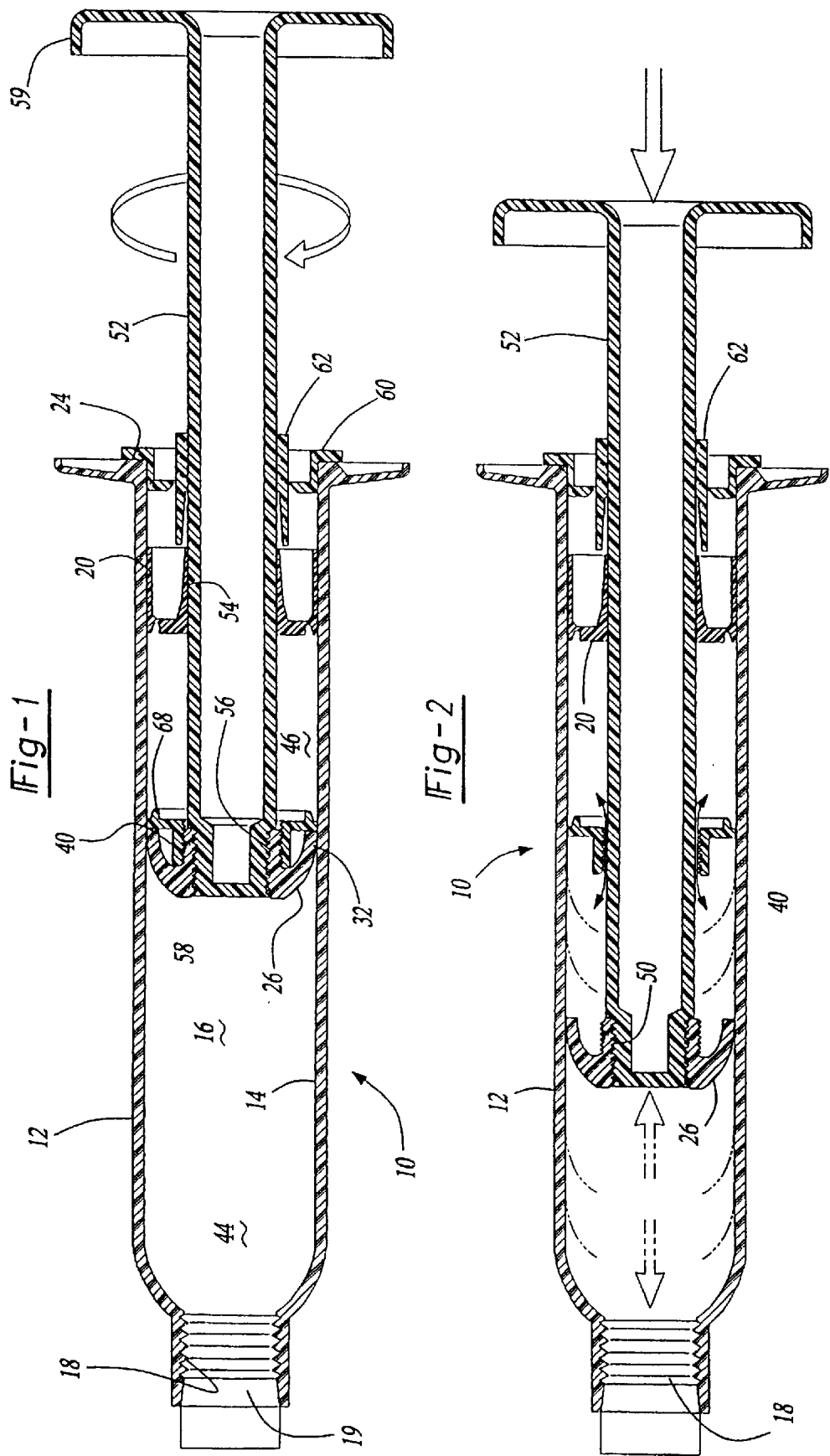

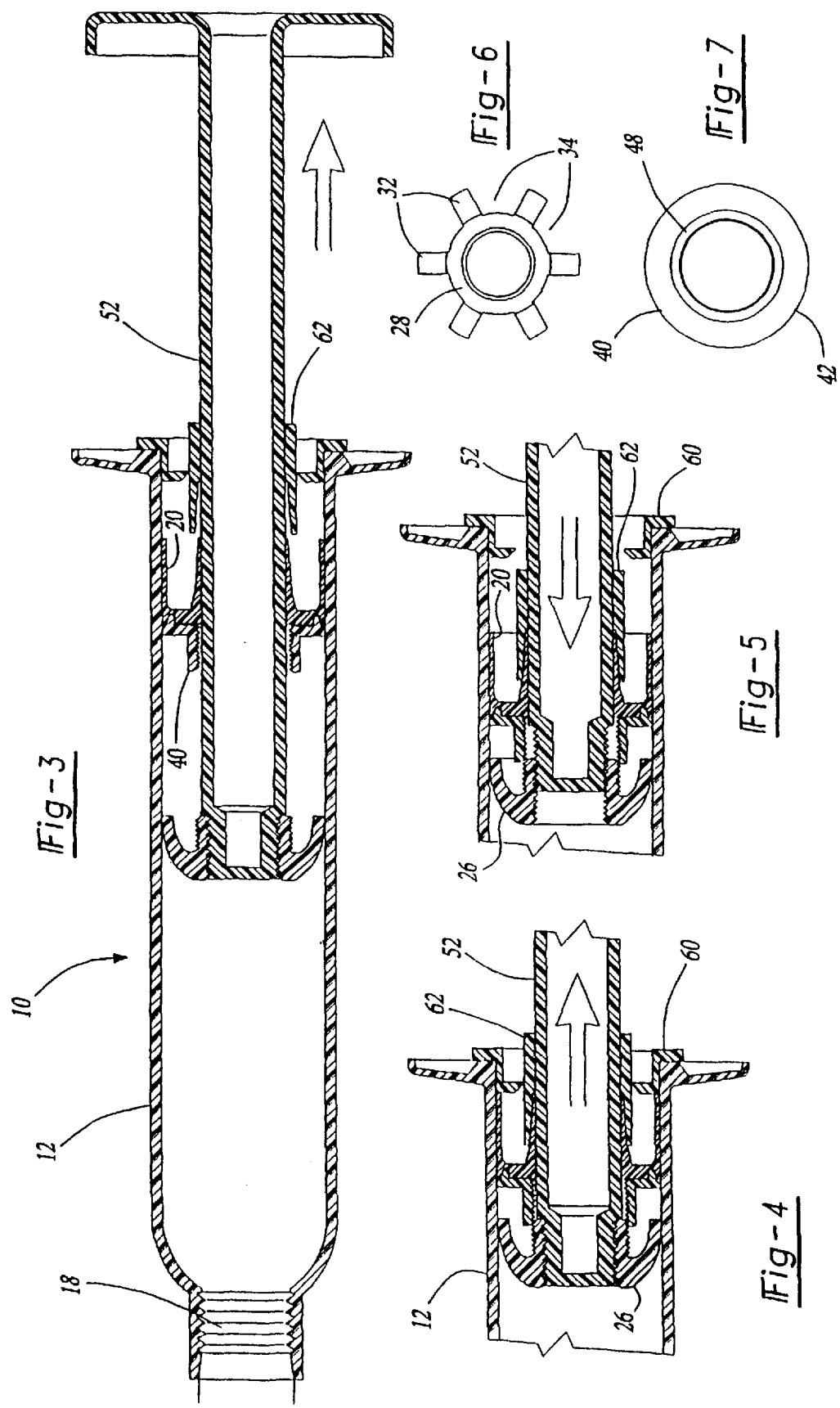

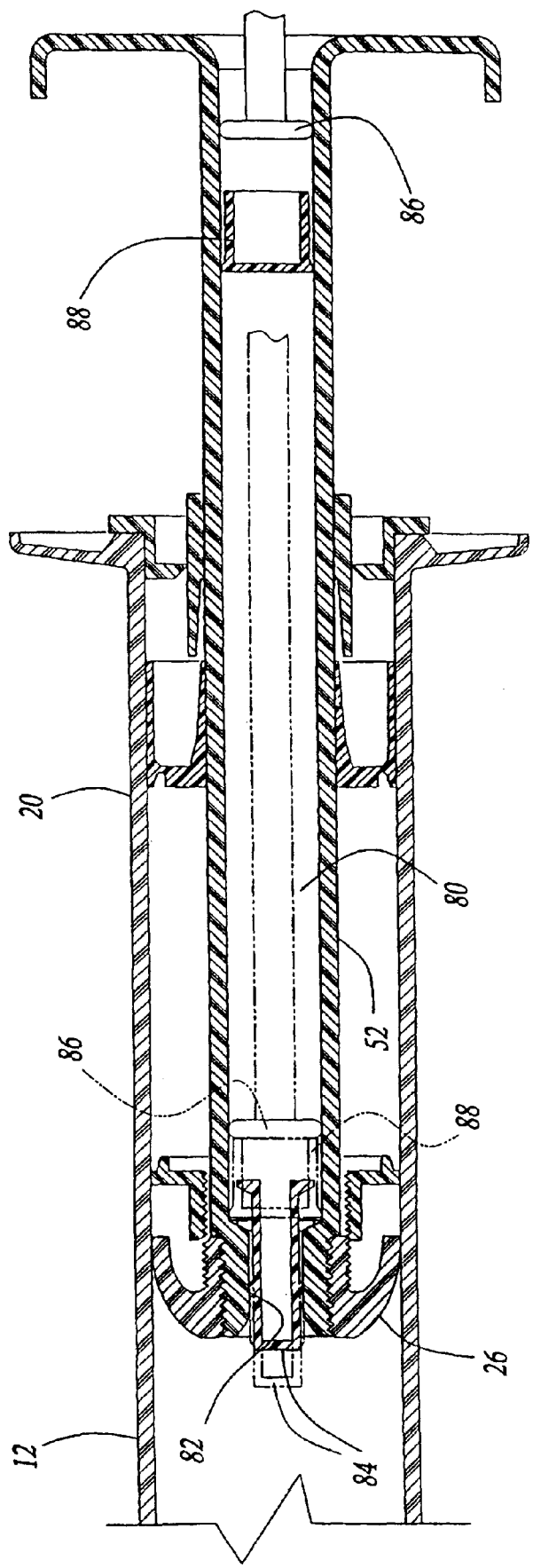

MULTIPLE PART MANUAL DISPENSING SYRINGE

This application claims the benefit of Provisional Application No. 60/062,846, filed Oct. 20, 1997.

BACKGROUND OF THE INVENTION

I. Field of the Invention

The present invention relates to a multiple-part dispensing syringe.

II. Description of the Prior Art

There are many previously known dispensing syringes for dispensing epoxy, polyurethane and other multi-part solutions.

These previously known syringes typically comprise an elongated tube which defines an elongated cylindrical chamber. A dispensing opening is formed at one end of the chamber while an axially slidably mounted plunger is initially positioned at the opposite end of the tube chamber.

A dasher is conventionally positioned within the tube chamber at a point intermediate the plunger and the dispensing opening. An elongated rod then extends through the dispensing opening and is detachably secured to the dasher. The dasher itself contains a plurality of axial openings formed through it and the rod is used to axially displace the dasher within the interior tube chamber in order to intermix the contents of the tube chamber.

These previously known multi-part dispensers are used to dispense adhesives, sealants, and the like, consisting of a base and catalyst which, once intermixed together, chemically react and harden. Epoxies and polyurethanes are examples of such mixtures.

Since the multiple parts of the solutions chemically react when mixed, it is necessary to maintain the two parts fluidly separated from each other until use of the dispenser material is desired. In order to accomplish this, these previously known dispensers typically utilize a foil barrier between the catalyst and the base which is punctured when use of the material is desired. This previous design, however, is disadvantageous since it may leave portions of the foil barrier floating within the mixed material.

Some other previously known two-part dispensers provide a combination dasher/barrier positioned at a mid point within the tube chamber. In order to retain the barrier in position, tape is provided around the exterior of the tube to retain the barrier in place.

The disadvantage of this type of previously know dispenser is at the removal the tape is not only complicated, but also contributes waste. Furthermore, the previously known dispensers of this type require a tight seal between the dasher and the interior of the tube which in turn requires a high mixing force to be applied to the dasher rod to axially displace the dasher and intermix the catalyst and base.

A still further disadvantage of these previously known dispensers is that, after the materials have been intermixed by reciprocating the dasher via the rod within the interior of the tube chamber, the rod is detached from the dasher and discarded. This operation is not only messy but also contributes undesirable waste. Current dispensers require a device, mechanical or pneumatically, to expel mixed material out. Current syringe has a very small opening (0.090 diameter) which contributes to the difficulty of tip filling and the problem of air entrapment. In addition, the current syringe only comes with a luer-lock feature which limits the number of dispensing nozzles could be used.

SUMMARY OF THE PRESENT INVENTION

The present invention provides a multi-part dispenser which overcomes all of these previously known disadvantages of the previously known devices.

In brief, the dispensing syringe of the present invention comprises an elongated cylindrical tube defining a cylindrical interior chamber having a dispensing opening at one end. A plunger is axially slidably mounted within the tube and is initially positioned at the end of the chamber opposite from the dispensing end. A cylindrical dasher is positioned within the chamber at an intermediate point between the plunger and the dispensing opening. The dasher includes at least one axial opening formed through it.

A cylindrical barrier is threadably detachable secured to the dasher on its axial ends facing the plunger. Consequently, with the dasher and barrier positioned together, the dasher and barrier sealingly engages the inner periphery of the tube chamber and divides the tube chamber into two subchambers, one to receive the catalyst and the other to receive the base.

An elongated-rod extends through registering openings in the barrier and plunger and has one end secured to the dasher. The opposite end of the rod extends outwardly from the plunger end of the tube.

When use of the dispenser is required, the rod, which attached to the dasher, is rotated clockwise to separate the dasher from the barrier. In doing so, fluid communication is established between the two tube subchambers through the openings formed both through the dasher and the barrier as well as the space between the barrier and dasher following their separation.

The rod is then used to push the dasher and barrier towards the plunger where the barrier will nest on the plunger due to the mating of two surfaces. The barrier will maintain the contact with the plunger complementary to the friction between the barrier OD and syringe ID. Thereafter, the dasher is used to intermix materials formerly contained within the two subchambers in the conventional fashion.

After the materials within the tube subchambers are completely intermixed, the rod with its attached dasher is retracted outwardly from the tube and until the dasher abuts against the barrier which is already positioned against the plunger. Once the rod is fully retracted in the tube, complementary wedging surfaces on both the plunger as well as the cylindrical locking sleeve coaxially positioned around the plunger frictionally locks the rod and plunger together. Thereafter, the now interlocked rod, plunger, barrier and locking sleeve are used to dispense the material within the tube out of the dispensing end of the tube.

BRIEF DESCRIPTION OF THE DRAWING

A better understanding of the present invention will be had upon reference to the following detail description when read in conjunction with the accompanying drawing, wherein like reference characters refer to like parts throughout the several views, and in which:

FIG. 1 is a longitudinally sectional view illustrating a preferred embodiment of the present invention prior to intermixing the base and the catalyst;

FIG. 2 is a view similar to FIG. 1 but illustrating the initiation of the mixing process;

FIG. 3 is similar to FIG. 2 but illustrating the invention after mixing has begun;

FIGS. 4 and 5 are fragmentary sectional views illustrating the invention near the end of the mixing operation;

FIG. 6 is an end view of the dasher;

FIG. 7 is an end view of the barrier;

FIG. 9 is longitudinal sectional view illustrating a second preferred embodiment of the invention.

DETAILED DESCRIPTION OF A PREFERRED EMBODIMENT OF THE PRESENT INVENTION

Figure 8:
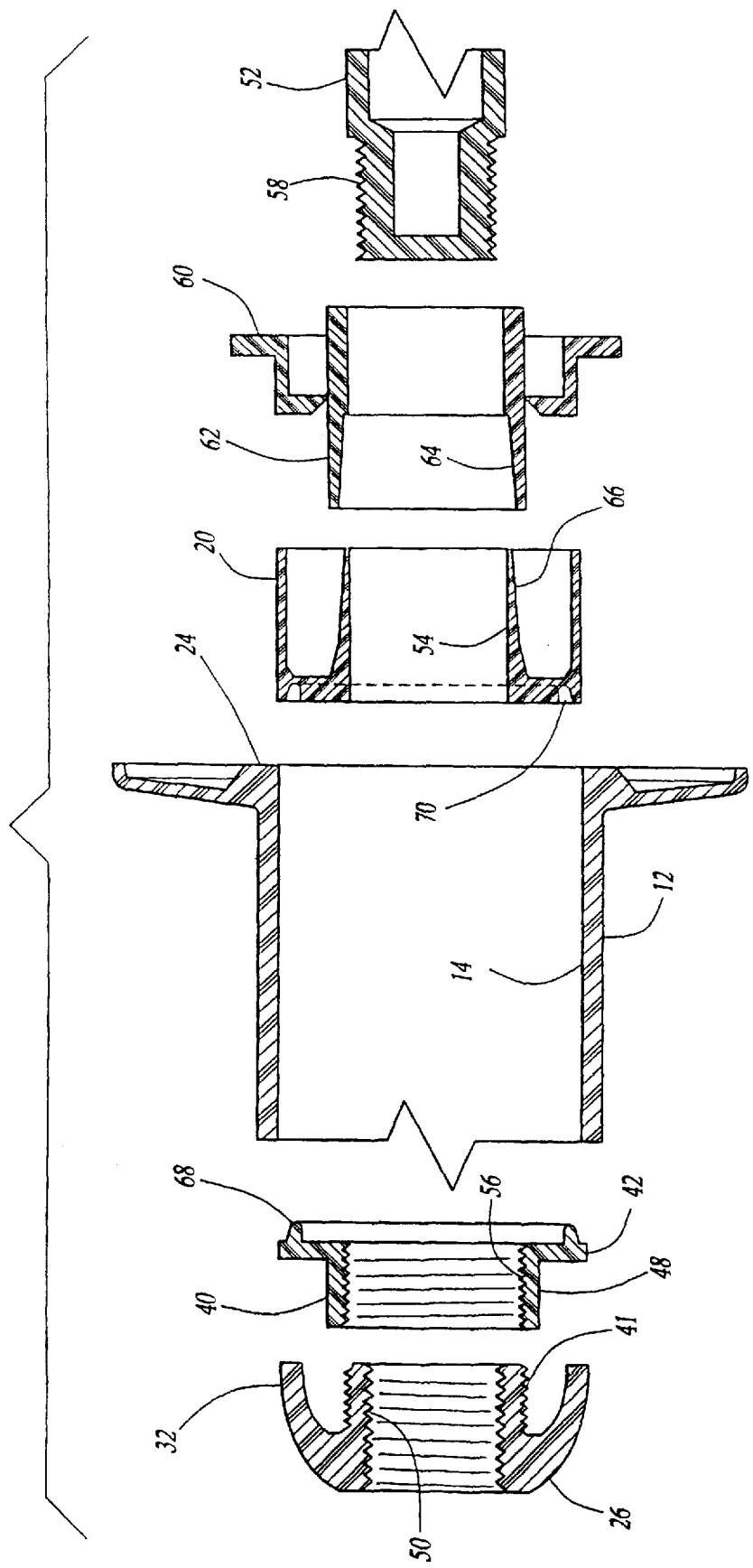
FIG. 8 is an exploded view illustrating the present invention.

With reference first to FIGS. 1 and 8 of the drawing, a preferred embodiment of the two-part dispenser 10 of the present invention is there shown and comprises an elongated cylindrical tube 12. The interior walls 14 of the tube define an elongated cylindrical chamber 16 having a dispensing opening 18 at one end. Preferably, the opening 18 is internally pipe threaded as shown at 19 to receive a complementary externally threaded dispensing tip.

A cylindrical plunger 20 is longitudinally slidably mounted within the tube chamber 16 and such that its outer periphery sealingly engages the inner wall 14 of the tube 12. In its initial position shown in FIG. 1, i.e., prior to dispensing of the material contained within the tube chamber 16, the plunger 20 is positioned at an end 24 of the tube 12 opposite from the dispensing opening 18.

With reference now to FIGS. 1, 8 and 6, a cylindrical dasher 26 is positioned at an intermediate point in the housing chamber 16 between the plunger 20 and dispensing opening 18. The dasher 26 generally comprises a cylindrical central hub 28 (FIG. 6) having a plurality of radially outwardly extending spokes 32. The spokes 32, furthermore, are circumferentially spaced apart from each other thus forming openings 34 between adjacent spokes 32.

Referring now particularly to FIGS. 1, 7, and 8, a generally cylindrical barrier 40 is provided adjacent the dasher 26 between the dasher 26 and the end 24 of the tube 12. The dasher 26 includes external threads 41 (FIG. 8) which threadably engages internal threads on the barrier 40 to detachably secure the dasher 26 and barrier 40 together and, in doing so, the facial contact and threaded connection between the dasher 26 and barrier 40 maintains a fluid seal. A circular outer periphery 42 of the barrier 40 sealingly engages the interior wall 14 of the tube 12 thus dividing the tube chamber 16 into two axially adjacent subchambers 44 and 46.

An tubular flange 48 on the barrier 40 is sealingly positioned around (FIG. 1) an annular boss 50 (FIG. 2) formed on the dasher 26 in order to frictionally secure the dasher 26 and barrier 40 together. Furthermore, the seal between the flange 48 and the boss 50 is fluid tight so that, with the dasher 26 and barrier 40 secured together as shown in FIG. 1, a fluid seal is maintained between the tube subchambers 44 and 46.

Still referring to FIGS. 1 and 8, an elongated rod 52 extends through registering bores 54 and 56 (FIG. 8) in the plunger 20 and barrier 40, respectively, and has one end 58 secured to the dasher 26 by any conventional means, such as threads. The opposite end 61 of the rod 52 extends outwardly from the end 24 of the tube 12 and has a push handle 59. Furthermore, the length of the rod 52 is preferably substantially the length of the tube 12.

Still referring to FIGS. 1 and 8, a cylindrical closure 60 is disposed across the end 24 of the tube 12. The closure 60 supports an elongated tubular and cylindrical locking sleeve 62 such that the locking sleeve 62 is circumferentially disposed around the rod 52. However, only a frictional or frangible connection is provided between the closure 60 and the locking sleeve 62 for a reason to be shortly described.

As best shown in FIG. 8, the locking sleeve 62, furthermore, includes a flared conical surface 64 at its end facing the plunger 20. The plunger 20, in turn, includes a conical surface 66 which faces the conical surface 64 of the sleeve 62 and the conical surfaces 54 and 64 are complementary to each other. Furthermore, the conical surfaces 66 and 64 both form wedging surfaces and are initially axially spaced apart from each other as shown in FIG. 1.

The component parts of the present invention having been described, its operation is as follows:

With reference first to FIG. 1 and with the dasher 26 and barrier 40 threadably secured together, the dasher 26 and barrier 40 combination divide the tube subchambers 16 into two subchambers 44 and 46 as has been previously described. Thus, the base and catalyst contained within the subchambers 44 and 46 are both physically and chemically separated from each other.

With reference now to FIG. 2, in order to intermix the base and catalyst together, the rod 52 is rotated clockwise to unscrew or separate the dasher from the barrier. In doing so, fluid communication between the subchambers 44 and 46 is established through the spaces 34 (FIG. 6) between the dasher spokes 32, the space between the dasher 26 and the barrier 40 as well as the central opening 56 on the barrier 40.

With reference now to FIGS. 3 and 8, after the dasher 26 and barrier 40 have been separated, the rod 52 is retracted thus pushing the barrier 40 against the plunger 20. In doing so, an annular flange 68 (FIG. 8) on the barrier 40 engages a receiving recess 70 formed on the plunger 20. Thereafter, the rod 52 is used to reciprocate and rotate clockwise the dasher 26 within the interior of the tube 12 thus intermixing the contents of the tube 12 in the desired fashion.

With reference to FIG. 4, after the contents of the tube 12 have been intermixed, the rod 52 is fully retracted outwardly from the tube 12 to the position shown in FIG. 4. In doing so, the dasher 26 abuts against the barrier 40 and in turn forces the plunger 20 axially outwardly towards the end 24 of the tube 12. In doing so, the wedging surface 66 on the plunger 20 engages the wedging surface 64 on the sleeve 62 and causes the plunger 20 to deflect radially inwardly towards the rod 52 thus griping the rod 52. In doing so, the rod 52, plunger 20 and sleeve 62 are frictionally locked together.

As shown in FIG. 5, after the rod 52, sleeve 62 and plunger 20 are locked together, the rod 52 is then axially displaced into the tube 12 towards the dispensing end 18 in order to dispense the now mixed material within the tube 12 out through the dispensing end 18 of the tube 12. Following completion of the dispensing operation, the entire assembly, i.e., the tube 12 together with the rod 52 and its attached components, are simply discarded.

Consequently, it can be seen that a primary advantage of the present invention is that is completely eliminates the previously known need to detach the rod 52 from the dasher and then separately discard of the rod 52.

With reference now to FIG. 9, a modification of the present invention is there shown for mixing three different liquids. As before, two of the liquids are contained within the subchambers 44 and 46 and separated from each other by the dasher 26 and barrier 40 combination. As such, the description thereof is unnecessary.

Unlike the first embodiment of the invention, however, in the second embodiment of the invention, the tube 52 is hollow thus defining a rod chamber 80 in which a third liquid is contained. An opening 82 is formed between the end of the rod 52 connected to the dasher 26 and the tube subchamber 44.

In order to prevent premature mixing of liquid contained within the rod chamber 80 and the tube subchamber 44, either a one-way valve or frangible barrier 84 is provided across the opening 82. The one-way valve or frangible barrier 84 fluidly seals the rod chamber 80 from the tube subchamber 44.

A plunger rod 86 is disposed within the rod chamber 80 at the end opposite from the dasher 26. Thus, to intermix the contents of the rod chamber 80 with the subchamber 44, the plunger rod 86 is axially displaced which axially moves a plunger 88 into the rod 52 thus flowing the material within the rod chamber 80 into the subchamber 44 in the desired fashion.

From the foregoing, it can be seen that the dispenser of the present invention is not only simple yet effective in operation, but also economical in construction. Preferably, all of the components of the dispenser are of a plastic construction.

Having described our invention, however, many modifications thereto will become apparent to those skilled in the art to which it pertains without deviation from the spirit of the invention as defined by the scope of the appended claims.

We claim:

1. A dispensing syringe comprising:

an elongated tube defining a cylindrical interior chamber having an internally threaded dispensing opening at one end of said chamber and a large opening at an other end of said chamber, a finger grip flange at the large opening of the syringe, a plunger axially slidably mounted in said tube, said plunger being positioned at the other end of said chamber, a cylindrical dasher positioned in said chamber intermediate said plunger and said dispensing opening, said dasher having at least one axial through opening, a cylindrical barrier, said barrier comprising internal threads and said dasher comprising external threads on the side of said dasher facing said plunger, wherein said barrier closes said axial through opening, said barrier together with said dasher sealingly engage said chamber thereby dividing said tube chamber into two subchambers, and said barrier is adapted to fluidly connect said subchambers, and an elongated rod, said rod secured at one end to said dasher, said rod extending through registering bores in said barrier and said plunger so that a second end of said rod extends exteriorly of said tube, and means for selectively locking said rod to said plunger when said rod retracts said barrier against said plunger.

2. The invention as defined in claim 1 wherein said barrier includes at least one axial through opening.

3. The invention as defined in claim 1 wherein said internal threads and external threads form complementary annular mating surfaces on said dasher and said barrier.

4. The invention as defined in claim 1 wherein said barrier is positioned between said dasher and said plunger.

5. The invention as defined in claim 1 wherein said plunger includes a circumferentially extending wedge surface at an end of said plunger facing outwardly from said chamber, and wherein said selective locking means comprises a sleeve coaxially positioned around said rod, said sleeve having a circumferentially extending wedge surface complementary to and facing said plunger wedge surface whereby, when said rod and barrier force said wedge surfaces together, said sleeve, rod and plunger are frictionally locked together.

6. The invention as defined in claim 5 wherein said wedge surfaces are each conical surfaces.

7. The invention as defined in claim 1 and comprising means for securing said barrier and said plunger together after detachment of said barrier from said dasher.

8. The invention as defined in claim 7 wherein said means for securing said barrier and said plunger together comprises complementary mating surfaces formed on said barrier and said plunger.

9. The invention as defined in claim 1 wherein said dasher is of a one piece plastic construction constructed with or without the hole in the center.

10. The invention as defined in claim 1 wherein said barrier is of a one piece plastic construction.

11. The invention as defined in claim 1 wherein said rod has an axial length at least twice as long as an axial length of said tube chamber.

12. The invention as defined in claim 1 wherein said rod is hollow thereby forming a rod chamber and comprising one way valve means between said rod chamber and said tube chamber at said one end of said rod.

13. The invention as defined in claim 1 wherein said rod is hollow thereby forming a rod chamber, said tube having an opening between said rod chamber and said tube chamber at said one end of said rod, and frangible barrier means disposed across said rod opening.

* * * * *